(12) United States Patent
Drukker et al.

(10) Patent No.: US 6,855,114 B2
(45) Date of Patent: Feb. 15, 2005

(54) AUTOMATED METHOD AND SYSTEM FOR THE DETECTION OF ABNORMALITIES IN SONOGRAPHIC IMAGES

(76) Inventors: Karen Drukker, 1337 W. Fargo Ave. #7C, Chicago, IL (US) 60626; Maryellen L. Giger, 265 Claremont, Elmhurst, IL (US) 60126; Karla Horsch, 1118 S. Ahrens, Lombard, IL (US) 60148; Carl J. Vyborny, 171 Michaux Rd., Riverside, IL (US) 60546

(*) Notice: Subject to any disclaimer, the term of this patent is extended or adjusted under 35 U.S.C. 154(b) by 24 days.

(21) Appl. No.: 10/126,523

(22) Filed: Apr. 22, 2002

(65) Prior Publication Data

US 2003/0125621 A1 Jul. 3, 2003

Related U.S. Application Data

(60) Provisional application No. 60/332,005, filed on Nov. 23, 2001.

(51) Int. Cl.$^7$ ................................................ A61B 8/00
(52) U.S. Cl. ...................................................... 600/443
(58) Field of Search ................................ 600/437, 443, 600/425, 408, 439, 440, 442, 447, 407, 409; 382/125, 128, 132, 171–172, 190, 203, 224–225, 260; 128/915

(56) References Cited

U.S. PATENT DOCUMENTS

| | | | |
|---|---|---|---|
| 5,572,597 A | * | 11/1996 | Chang et al. ............... 382/125 |
| 5,598,481 A | * | 1/1997 | Nishikawa et al. .......... 382/130 |
| 5,732,121 A | * | 3/1998 | Takeo et al. .................. 378/62 |
| 5,984,870 A | * | 11/1999 | Giger et al. ................. 600/443 |
| 5,987,094 A | * | 11/1999 | Clarke et al. ................. 378/62 |
| 6,138,045 A | * | 10/2000 | Kupinski et al. ............ 600/425 |
| 6,185,320 B1 | * | 2/2001 | Bick et al. ................... 382/132 |
| 6,317,617 B1 | * | 11/2001 | Gilhuijs et al. ............. 600/408 |
| 2001/0043729 A1 | * | 11/2001 | Giger et al. ................. 382/128 |
| 2002/0172403 A1 | * | 11/2002 | Doi et al. .................... 382/128 |

OTHER PUBLICATIONS

Kupinski, Automated Seeded Lesion Segmentation on Digital Mammograms, Aug. 1998, IEEE Transactions on Medical Imaging, vol. 17, No. 4.*

* cited by examiner

Primary Examiner—Ali Imam
(74) Attorney, Agent, or Firm—Oblon, Spivak, McClelland, Maier & Neustadt, P.C.

(57) ABSTRACT

A method of detecting a candidate abnormality in a sonographic medical image, based on determining a radial gradient index (RGI) at plural pixels, producing an RGI image, thresholding the RGI image, determining a candidate abnormality based on the thresholding step, and locating a center point of the candidate abnormality. The candidate abnormality may be classified by segmenting the candidate abnormality, including determining average radial gradients (ARDs) in the sonographic medical image based on the center point, extracting plural features from the segmented candidate abnormality, and determining a likelihood of the candidate abnormality being an actual abnormality based on the extracted plural features.

21 Claims, 15 Drawing Sheets

AUTOMATED METHOD AND SYSTEM FOR THE DETECTION OF ABNORMALITIES IN SONOGRAPHIC IMAGES

CROSS-REFERENCE TO RELATED APPLICATION

The present application claims priority to U.S. Provisional Patent Application 60/332,005 filed Nov. 23, 2001, entitled "Automated Method and System for the Detection of Abnormalities in Sonographic Images."

The present invention was made in part with U.S. Government support under grant number CA89452 and T31 CA09649 from the USPHS, and U.S. Army Medical Research and Materiel Command 97-2445.

BACKGROUND OF THE INVENTION

Field of the Invention

The invention relates generally to the field of computer-assisted diagnosis in the detection of abnormalities in sonography images. It describes a method and system that employ an abnormality detection module for the computer assisted interpretation of medical sonographic images. The technique includes background preprocessing, radial gradient processing, thresholding, and region growing. This technique is useful for analyzing abnormalities including, but not limited to, cysts, benign solid lesions, and malignant (cancerous) lesions.

The present invention also generally relates to computerized techniques for automated analysis of digital images, for example, as disclosed in one or more of U.S. Pat. Nos. 4,839,807; 4,841,555; 4,851,984; 4,875,165; 4,907,156; 4,918,534; 5,072,384; 5,133,020; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,832,103; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,138,045; 6,141,437; 6,185,320; 6,205,348; 6,240,201; 6,282,305; 6,282,307; 6,317,617 as well as U.S. patent application Ser. Nos. 08/173,935; 08/398,307 (PCT Publication WO 96/27846); 08/536,149; 08/900,189; 09/027,468; 09/141,535; 09/471,088; 09/692,218; 09/716,335; 09/759,333; 09/760,854; 09/773,636; 09/816,217; 09/830,562; 09/818,831; 09/842,860; 09/860,574; 60/160,790; 60/176,304; 60/329,322; 09/990,311; 09/990,310; 09/990,377; and 60/331,995; and PCT patent applications PCT/US98/15165; PCT/US98/24933; PCT/US99/03287; PCT/US00/41299; PCT/US01/00680; PCT/US01/01478 and PCT/US01/01479, all of which are incorporated herein by reference.

The present invention includes use of various technologies referenced and described in the above-noted U.S. Patents and Applications, as well as described in the references identified in the following LIST OF REFERENCES by the author(s) and year of publication and cross referenced throughout the specification by reference to the respective number, in parentheses, of the reference:

List of References

1. Sickles E A. Breast Imaging: From 1965 to the Present. *Radiology*, 151:1–16, 2000.
2. Warner E, Plewes D B, Shumak R S, Catzavelos G C, Di Prospero L S, Yaffe M J, Ramsay G E, Chart P L, Cole D E C, Taylor G A, Cutrara M, Samuels T H, Murphy J P, Murphy J M, and Narod S A. Comparison of Breast Magnetic Resonance Imaging, Mammography, and Ultrasound for Surveillance of Women at High Risk of Hereditary Breast Cancer. *J Clin Oncol*, 19:3524–3531, 2001.
3. Weber, W N, Sickles E A, Callen P W, and Filly R A. Nonpalpable Breast Lesion Localization: Limited Efficacy of Sonography. *Radiology*, 155:783–784, 1985.
4. Hilton S V, Leopold G R, Olson L K, and Wilson S A. Real-Time Breast Sonography: Application in 300 Consecutive Patient. *Am J Roentgenol*, 147:479–486, 1986.
5. Sickles E A, Filly R A, and Callen P W. Benign Breast Lesions: Ultrasound Detection and Diagnosis. *Radiology*, 151:467–470, 1984.
6. Velez N, Earnest D E, and Staren E D. Diagnostic and Interventional Ultrasound for Breast Disease. *Am J Surg*, 280:284–287, 2000.
7. Stavros A T, Thickman D, Rapp C L, Dennis M A, Parker S H, and Sisney G A. Solid Breast Nodules: Use of Sonography to Distinguish Between Benign and Malignant Lesions. *Radiology*, 196:123–134, 1995.
8. Rahbar G, Sie A C, Hansen G C, Prince J S, Melany M L, Reynolds H E, Jackson V P, Sayre J W, and Bassett L W. Benign Versus Malignant Solid Breast Masses: Use Differentiation. *Radiology*, 213:889–894, 1999.
9. Chen D -R, Chang R -F, and Huang Y -L. Computer-aided Diagnosis Applied to Use of Solid Breast Nodules by Using Neural Networks. *Radiology*, 213:407–412, 1999.
10. Buchberger W, DeKoekkoek-Doll P, Springer P, Obrist P, and Dunser M. Incidental Findings on Sonography of the Breast: Clinical Significance and Diagnostic Workup. *Am J Roentgenol*, 173:921–927, 1999.
11. Berg W A and Gilbreath P L. Multicentric and Multifocal Cancer: Whole Breast Use in Preoperative Evaluation. *Radiology*, 214:59–66, 2000.
12. Zonderland H M, Coerkamp E G, Hernans J, van de Vijver M J, and van Voorthuisen A E. Diagnosis of Breast Cancer: Contribution of Use as an Adjunct to Mammography. *Radiology*, 213:413–422, 1999.
13. Moon W K, Im J-G, Koh Y H, Noh D-Y, and Park I A. Use of Mammographically Detected Clustered Microcalcifications. *Radiology*, 217:849–854, 2000.
14. Bassett L W, Israel M, Gold R H, and Ysrael C. Usefulness of Mammography and Sonography in Women <35 Yrs Old. *Radiolography*, 180:831, 1991.
15. Kolb T M, Lichy J, and Newhouse J H. Occult Cancer in Women with Dense Breasts: Detection and Screening Use—Diagnostic Yield and Tumor Characteristics. *Radiology*, 207:191–199, 1998.
16. Giger M L, Al-Hallaq H, Huo Z, Moran C, Wolverton D E, Chan C W, and Zhong W. Computerized Analysis of Lesions in Use Images of the Breast. *Acad Radiol*, 6:665–674, 1999.
17. Garra B S, Krasner B H, Horii S C, Ascher S, Mun S K, and Zeman R K. Improving the Distinction Between Benign and Malignant Breast Lesions: The Value of Sonographic Texture Analysis. *Ultrason Imaging*, 15:267–285, 1993.
18. Chen D R, Chang R F, and Huang Y L. Computer-aided Diagnosis Applied to Use of Solid Breast Nodules by Using Neural Networks. *Radiology*, 213:407–412, 1999.
19. Golub R M, Parsons R E, Sigel B, and et el. Differentiation of Breast Tumors by Ultrasonic Tissue Characterization. *J Ultrasound Med*, 12:601–608, 1993.
20. Sahiner B, LeCarpentier G L, Chan H P, and et el. Computerized Characterization of Breast Masses Using Three-Dimensional Ultrasound Images. In *Proceedings of the SPIE*, volume 3338, pages 301–312, 1998.

21. Horsch K, Giger M L, Venta L A, and Vyborny C J. Computerized Diagnosis of Breast Lesions on Ultrasound. *Med Phys,* 2001. In press.
22. Kupinski M A and Giger M L. Automated Seeded Lesion Segmentation on Digital Mammograms. *IEEE Trans Med Im,* 17:510–517, 1998.
23. Horsch K, Giger M L, Venta L A, and Vyborny C J. Automatic Segmentation of Breast Lesions on Ultrasound. *Med Phys,* 28:1652–1659, 2001.
24. Tohno E, Cosgrove D O, and Sloane J P. *Ultrasound Diagnosis of Breast Disease.* Churchill Livingstone, Edinburgh, Scotland, 1994.
25. Kupinski M A, Edwards D C, Giger M L, and Metz C E. Ideal Observer Approximation Using Bayesian Classification Neural Networks. *IEEE Trans Med Im,* 20:886–899, 2001.
26. Metz C E. Basic Principles of ROC Analysis. *Sem Nucl Med,* 8:283–298, 1978.

The contents of each of these references are incorporated herein by reference. The techniques disclosed in the patents and references can be utilized as part of the present invention.

DISCUSSION OF THE BACKGROUND

Breast cancer is the leading cause of death for women in developed countries. Detection of breast cancer in an early stage increases success of treatment dramatically, and hence screening for breast cancer of women over 40 years of age is generally recommended. Current methods for detecting and diagnosing breast cancer include, for example, mammography, sonography (also referred to as ultrasound), and magnetic resonance imaging (MRI). Mammography is the standard method used for periodic screening of women over 40 years of age. MRI has recently gained interest as a breast cancer screening tool (See Reference 2), but has not been used widely.

In the mid 1980's, sonography gained recognition as an imaging tool for breast cancer, but at that time the results were disappointing, both for localization (See Reference 3) and screening (See Reference 4). Sonography is currently the method of choice to distinguish simple cysts of the breast from solid abnormalities (See Reference 5), while most radiologists still feel uncomfortable relying on sonography to differentiate solid masses. The use, however, of diagnostic and interventional sonography for breast cancer has grown rapidly over the last few years (See Reference 6). Recently, several groups have shown that sonography may be used for classification of solid benign and malignant masses (See References 7 and 8). It has also been shown that the use of computer classification schemes for the distinction between benign and malignant masses helped inexperienced operators avoid misdiagnosis (See Reference 9).

The merits of sonography as an adjunct to mammography have been explored. Sonography is especially helpful for detection of otherwise occult malignancies in young women with dense breasts (See Reference 10) and for preoperative evaluation, particularly when breast conservation is considered (See Reference 11). Another study showed that the use of sonography as an adjunct to mammography results in a relevant increase in the diagnostic accuracy (See Reference 12). Sonography was also shown to be helpful in the detection of masses associated with mammographically detected microcalcifications (See Reference 13).

Mammograms of younger women are often hard to interpret. Sonography was shown to be more effective than mammograms for women younger than 35 (See Reference 14), and to be able to achieve similar general effectiveness as mammography for older women. A study of the effectiveness of sonography as a screening tool for women with dense breasts examined more than 11,000 consecutive patients (See Reference 15). All of the women selected for sonography were women with dense breasts and normal mammographic and physical examinations (more than 3,000). The use of sonography increased overall cancer detection by 17%. It was shown that sonography is able to depict small, early-stage, otherwise occult malignancies, similar in size and stage as those detected by mammography, and smaller and lower in stage than palpable cancers in dense breasts.

This illustrates the potential of sonography as a screening tool. A fundamental issue in the detection of abnormalities in breast tissue is the level of difficulty in performing a correct diagnosis. Previously, the diagnosis of breast tissue in sonographic images was very operator dependent. It required highly intensive operator training. Consequently, there are no standard methods for diagnosing an abnormality in breast tissue for a sonographic image.

SUMMARY OF THE INVENTION

Accordingly, an object of this invention is to provide a method, system, and computer program product for the automated detection of abnormalities in medical sonographic images, including using a Bayesian neural network (BNN) to determine the likelihood of a true abnormality versus false positive (FP) detection.

This and other objects are achieved by way of a method, system, and computer program product constructed according to the present invention, wherein a candidate abnormality is detected in a medical image and diagnosed as either a true abnormality or as a false detection. One such medical image environment is breast sonograms.

In particular, according to one aspect of the present invention, there is proved a novel method for detecting a candidate abnormality in a sonographic medical image, based on determining a radial gradient index (RGI) at plural pixels, producing an RGI image, thresholding the RGI image, determining a candidate abnormality based on the thresholding step, locating a center point of the candidate abnormality, segmenting the candidate abnormality including determining average radial gradients (ARDs) (See Reference 21) in the sonographic medical image in relation to the center point, extracting plural features from the segmented candidate abnormality, and determining a likelihood of the candidate abnormality being an actual abnormality based on the extracted plural features.

According to other aspects of the present invention, there are provided a novel system implementing the method of this invention and a novel computer program product, which upon execution causes the computer system to perform the above method of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
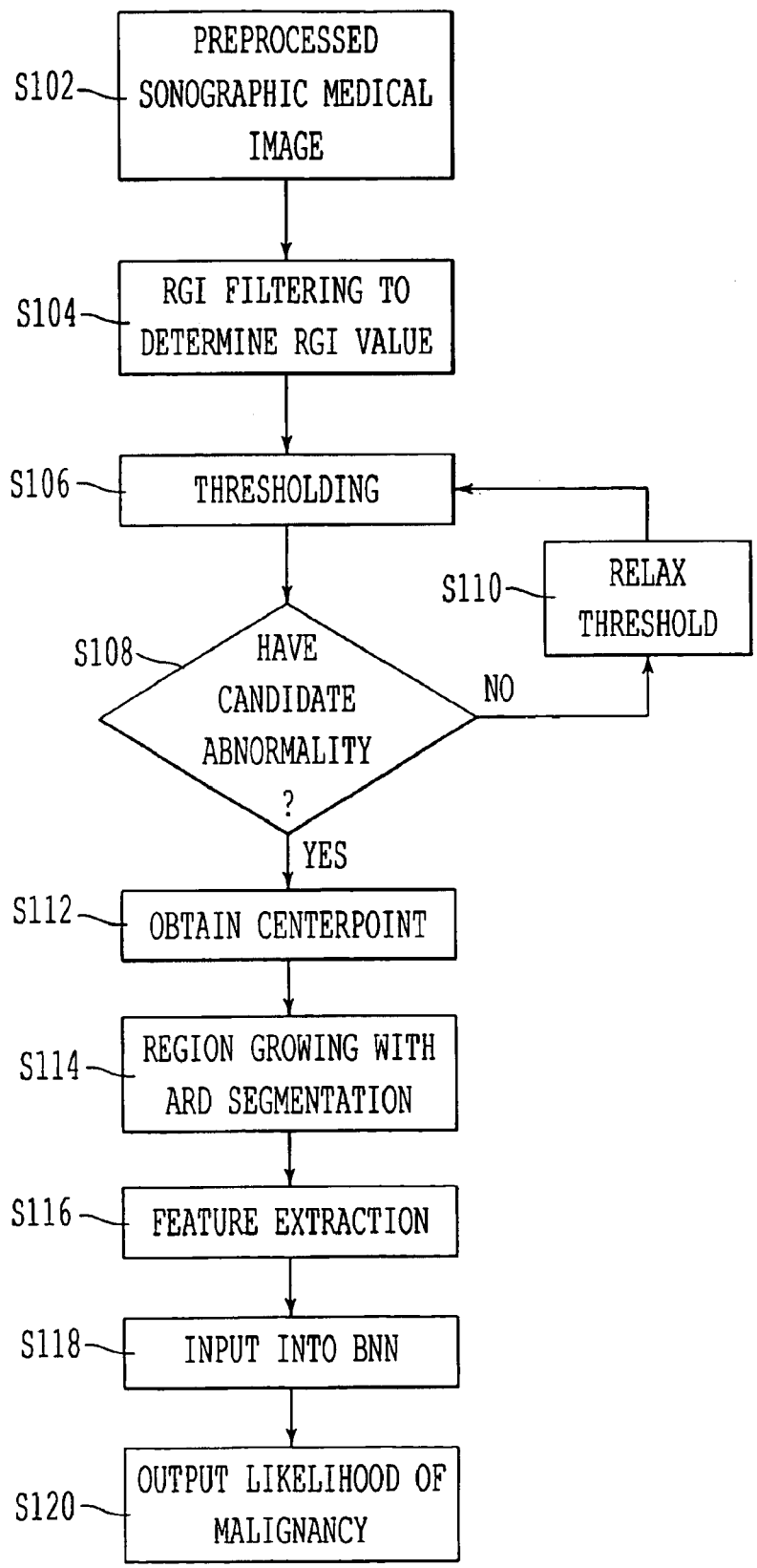
FIG. 1 illustrates the method for computer detection of abnormalities in sonographic images.

Referring now to the drawings, wherein like reference numerals designate identical or corresponding parts throughout the several views, as described herein, the inventors discovered that a Bayesian neural network provides a likelihood of true abnormality that closely corresponds to a radiologist's diagnosis. During diagnostic breast exams at the Lynn Sage Breast Center of Northwestern Memorial Hospital, 757 images were obtained from 400 consecutive sonography examinations. The images were obtained using an ATL 3000 unit and were captured directly from the 8-bit video signal. The number of images available per patient varied from one to six. The cases were collected retrospectively and had been previously diagnosed (i.e., by biopsy or by aspiration). Of the 400 sonographic cases, 124 were complex cysts (229 images), 182 were benign solid lesions (334 images), and 94 were malignant solid lesions (194 images).

In order to obtain initial indicators of the performance of the methods described herein, 36 "normal" images were constructed from images in the database that contained substantial normal areas. The average image size of the "normal" images was smaller than the average overall image size by approximately a factor of 3 (384 mm$^2$ as compared with 1120 mm$^2$).

As shown in FIG. 1, the detection of abnormalities in sonographic images includes obtaining a preprocessed image, automated pixel-based radial gradient filtering (RGI filtering), and ARD segmentation. In sonographic images, abnormalities are almost invariably darker than the background, thus the image gray scale is inverted prior to RGI filtering. The size of the sonography images varies, as well as the pixel size. The average image area is 1120 mm$^2$, while the image height ranges from 15 mm to 48 mm. The average pixel size equals 96 microns. In order to suppress the sonographic speckle, the images are pre-filtered using a square median filter with a side of 0.95 mm. Images thus pre-processed, as shown in step S102, form the input to the RGI filtering technique of step S104. In order to speed up the RGI-filtering, the preprocessed images are subsampled with a factor of 4. The threshold for the RGI filtered image is varied step-wise from 0.74 to 0.66, until at least one area of interest is detected, in steps S106, S108, and S110. Detected areas smaller than 5 mm$^2$ are discarded, since those are likely due to artifacts.

The filtering technique of step S104 for abnormality detection is based on the radial gradient index (RGI) of computer-generated contours of candidate abnormalities. (See Reference 22). Abnormality-like shapes are obtained by first multiplying the image with a constraining function, a two-dimensional (2D) isotropic Gaussian, having a width of 15 mm, using the following equation for a 2D homogeneous Gaussian centered at $(\mu_x, \mu_y)$:

$$RGI_1(\mu_x, \mu_y) = \frac{1}{\sum_{(x,y) \in C_i} |\vec{g}(x,y)|} \sum_{(x,y) \in C_i} \vec{g}(x,y) \cdot \hat{r}(x,y), \quad (1)$$

Here, $\vec{g}(x,y)$ is the gradient vector, $|\vec{g}(x,y)|$ its length, and $\hat{r}(x,y)$ the unit radial vector pointing from $(\mu_x, \mu_y)$ to (x,y). By definition, RGI values are between −1 and +1, where an RGI value of +1 signifies that along the contour all gradients point radially outward, and where an RGI value of −1 means that all gradients point radially inward. Actual abnormalities are expected to have absolute RGI values of close to 1. For a given image point $(\mu_x, \mu_y)$, the contour with the maximum RGI value is selected and this value is assigned to the $(u_x, u_y)$ coordinate in the filtered image. The RGI filtered image subsequently undergoes thresholding in step S106 to determine regions of interest (ROIs), such as candidate abnormalities, in step S108. If no candidate abnormality has been detected in step S108, the threshold is relaxed in step S110 and thresholding in step S106 is repeated. Steps S110 and S106 are repeated until the output of step S108 is "yes," indicating that a candidate abnormality has been detected.

For all detected areas, the geometric center is determined in step S112, and stored for later use in abnormality segmentation. The image gray level data is denoted by I(m,n) where m=(0,1, . . . ,M$_I$−1) and n=(0,1, . . . ,N$_I$−1). M$_I$ is the number of pixels in the lateral direction of the image and N$_I$ is the number of pixels in the depth direction of the image. The gradient image is denoted by ∇I and is computed using Sobel filters. The gray level data of a subimage, or ROI, is denoted by R(m,n) where m=(0, 1, . . . M$_R$−1) and n=(0, 1, . . . , N$_R$−1). M$_R$ is the number of pixels in the lateral direction of the ROI and N$_R$ is the number of pixels in the depth direction of the ROI. The points on the candidate abnormality margin have x and y coordinates $(\gamma_1(j), \gamma_2(j))$ where the index j=(0,1, . . . ,J−1) and J is the number of points in the margin. A vector $\hat{r}(m,n)$ of unit length is also required in the radial direction from the geometric center of the candidate abnormality to the point indexed by (m,n).

The geometric center of the candidate abnormality is computed by:

$$(m_c, n_c) = \left( \frac{\sum_m \sum_n L(m,n) m}{A}, \frac{\sum_m \sum_n L(m,n) n}{A} \right) \quad (2)$$

where L(m,n) is the candidate abnormality mask, a binary image having value 1 within the image and 0 (zero) elsewhere. A is the area of the candidate abnormality.

After ROIs are located by RGI filtering and their centers are documented as points of interest, a region growing algorithm is applied to determine candidate abnormality margins, in step S114. (See Reference 23). In step S114, ARD is also used to segment. (See Reference 23).

In order to study the sensitivity of the segmentation algorithm on the choice of variance, both manual and automatic width and height estimation were performed. The segmentation algorithms using manually and automatically estimated candidate abnormality width and height are referred to as partially automatic and fully automatic, respectively.

In fully automated candidate abnormality segmentation using ARD, estimations of the candidate abnormality width and height are determined by Sobel edge detection.

If C is the constraint function to be used in ARD segmentation, then the resulting image is:

$$J(\hat{P}) = C(\hat{P}) * \left(1 - \frac{\tilde{I}(\hat{P})}{\max_{\hat{P}}(\tilde{I}(\hat{P}))}\right), \quad (3)$$

where $\hat{P}$ is the pixel location. Inverting the image changes the candidate abnormality from dark (low gray values) to light (high gray values). The constraint function should have higher gray values in the region of the candidate abnormality and gray values near zero far from the candidate abnormality. Here, a Gaussian is used as the constraint function. The Gaussian is centered at the manually defined candidate abnormality center, $\hat{\mu}$:

$$C(\hat{P}) = N(\hat{P}; \hat{\mu}, \hat{\sigma}) = \frac{\exp\left(-\frac{1}{2}(\hat{P}-\hat{\mu})^T K^{-1}(\hat{P}-\hat{\mu})\right)}{2\pi\sqrt{\det K}} \quad (4)$$

Here the covariance matrix is assumed diagonal, $$K = \begin{pmatrix} \sigma_x^2 & 0 \\ 0 & \sigma_y^2 \end{pmatrix}, \quad (5)$$

where $\sigma_x^2$ and $\sigma_y^2$ are the variances in the lateral and depth direction, respectively. The variances are chosen as $$\sigma_x = \frac{w}{2}, \quad \sigma_y = \frac{h}{2} \quad (6)$$

with w being the estimated candidate abnormality width and h being the estimated candidate abnormality height (or depth).

In partially automatic segmentation using ARD, a manual estimation of the candidate abnormality width and height is achieved using the manually delineated candidate abnormality margin. If $\gamma(i)=(\gamma_1(i),\gamma_2(i))$ is a discrete parametrization of the manually delineated margin with $\gamma_1$ and $\gamma_2$ being the coordinates in the lateral and depth direction, respectively, then, $$w_{manual} = \max_i(\gamma_1(i)) - \min_i(\gamma_1(i)), \quad (7)$$

$$h_{manual} = \max_i(\gamma_2(i)) - \min_i(\gamma_2(i)). \quad (8)$$

In fully automatic candidate abnormality segmentation, estimations of the candidate abnormality width and height are determined through Sobel edge detection. The Sobel filtered images are defined by $$\tilde{I}_x = F_x * \tilde{I},$$

$$\tilde{I}_y = F_y * \tilde{I}, \quad (9)$$

where $\tilde{I}$ is the preprocessed image, * is the convolution operator, and $F_x$ and $F_y$ are 3×3 Sobel filters in the lateral and depth direction, respectively, $$F_x = \begin{pmatrix} -1 & 0 & 1 \\ -2 & 0 & 2 \\ -1 & 0 & 1 \end{pmatrix}, \quad F_y = \begin{pmatrix} 1 & 2 & 1 \\ 0 & 0 & 0 \\ -1 & -2 & -1 \end{pmatrix}. \quad (10)$$

Estimations of the locations of the candidate abnormality edges along horizontal and vertical lines through the candidate abnormality center are given by $$x_0 = \arg\left(\min_{i\in[1,\mu_x]} \tilde{I}_x(i, \mu_y)\right), \quad (11)$$

$$x_1 = \arg\left(\max_{i\in[\mu_x,N_x]} \tilde{I}_x(i, \mu_y)\right),$$

$$y_0 = \arg\left(\min_{i\in[1,\mu_y]} \tilde{I}_x(\mu_x, i)\right),$$

$$y_1 = \arg\left(\max_{i\in[\mu_y,N_y]} \tilde{I}_x(\mu_x, i)\right).$$

The estimated locations of candidate abnormality edges are then used to estimate the candidate abnormality width and height by $$w_{automatic} = 2\min(\mu_x - x_0, x_1 - \mu_x), \quad (12)$$

$$h_{automatic} = 2\min(\mu_y - y_0, y_1 - \mu_y). \quad (13)$$

For the width, instead of using the length between the left and right edges, twice the minimum of the lengths between the candidate abnormality center and the left and right edges is used. This is done to avoid the overestimation that may result when distant pixels are mistaken for the candidate abnormality edge. The same prevention of overestimation is applied for automatic lesion height estimation. The candidate abnormality segmentation that results from using such estimation will err on the side of "under growing" rather than "over growing."

When $w_{automatic}$ and $h_{automatic}$ are used in Equation (4), the candidate abnormality center is the only information defined manually that is needed by the segmentation algorithm.

Figure 2A:
FIG. 2 is an illustration of each step of the computerized detection process: (a) the original image, (b) the gray-scale inverted and median filtered image, (c) the pixel-based, radial-gradient filtered image, (d) the thresholded image, (e) the average radial gradient image with suspect regions grown.
Figure 2B:
Figure 2C:
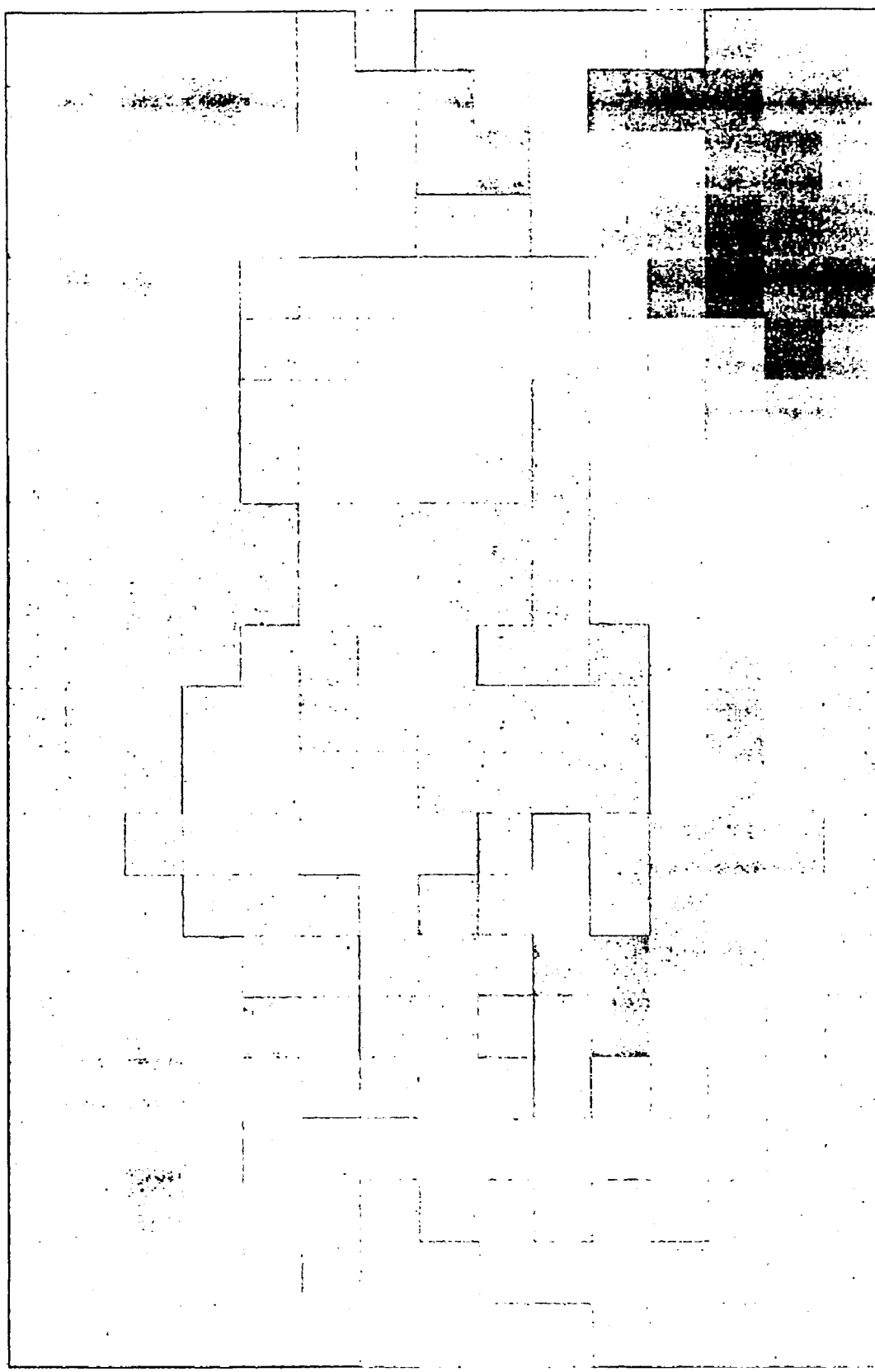
Figure 2D:
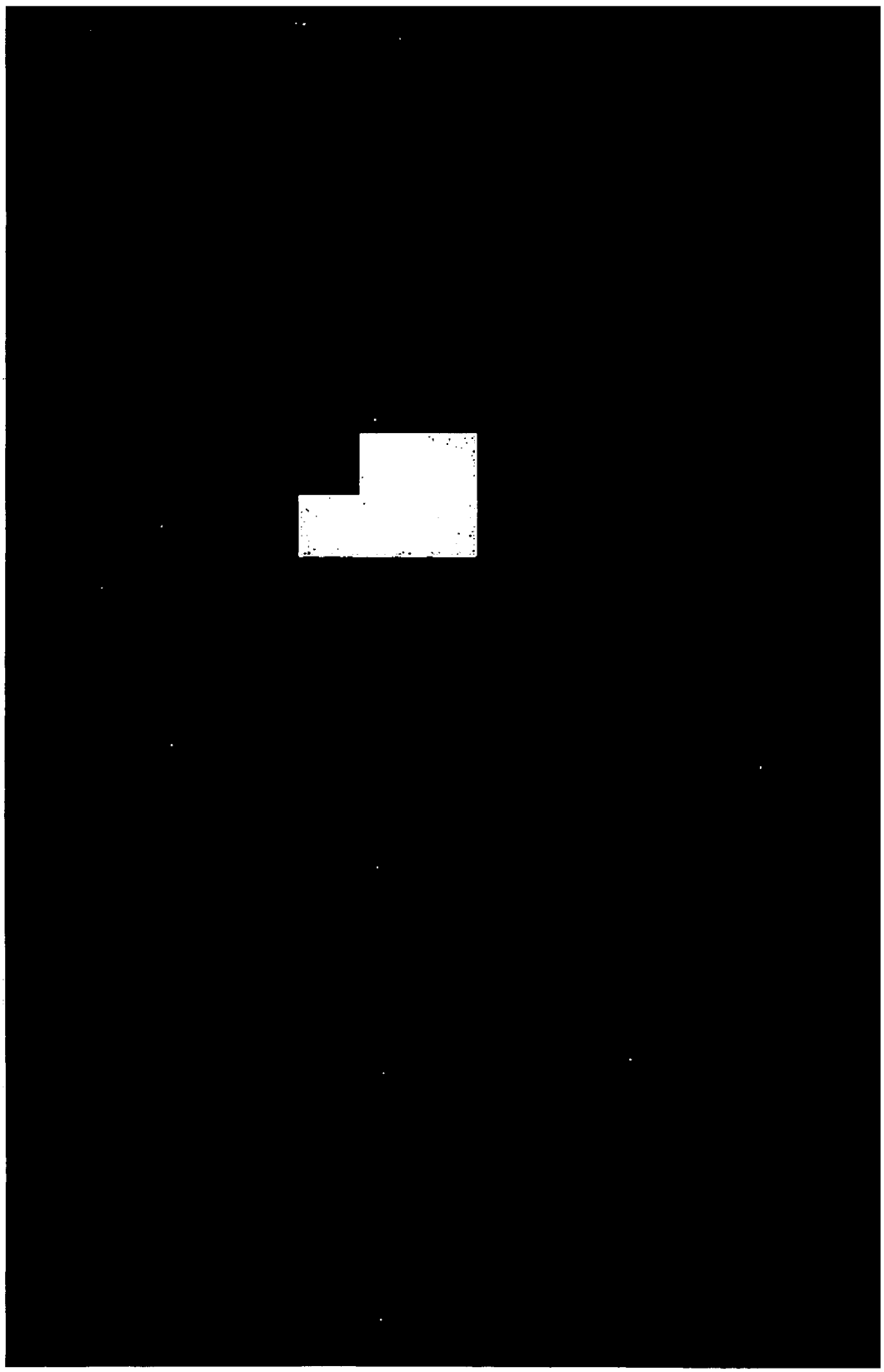
Figure 2E:
Figure 3A:
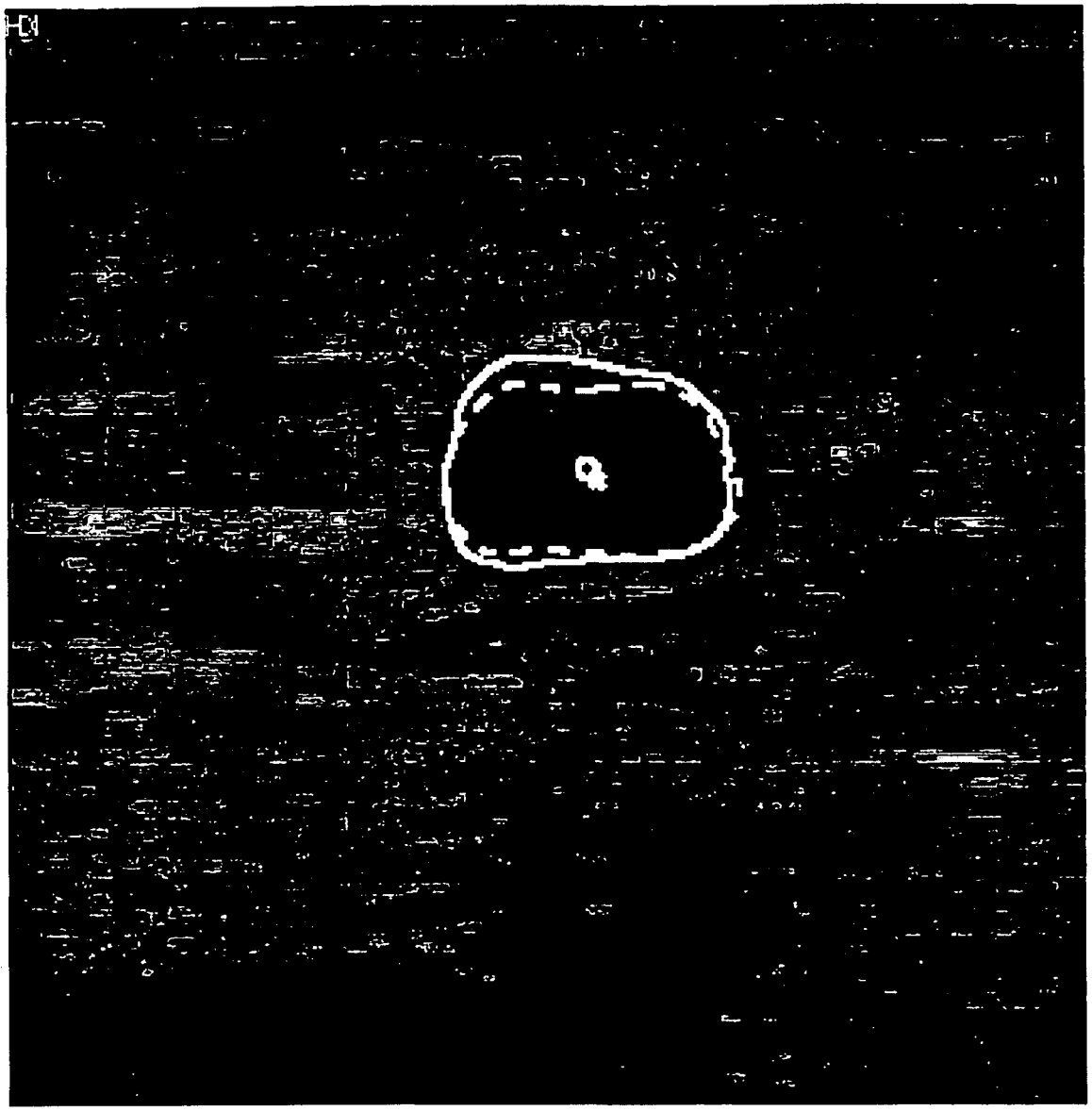
FIG. 3 shows examples of abnormality detection and then segmentation on sonographic images of the breast: (a) cyst, (b) benign solid mass, (c) malignant mass, (d) benign solid mass with false-positive detections, (e) malignant abnormality for which its shadow hinders detection and segmentation, (f) subtle malignant lesion that goes undetected (false-negative), (g) malignant lesion exhibiting substantial posterior acoustic shadowing resulting in a computer false-positive detection plus a false-negative, and (h) computer detection lies outside the radiologist outline, but the region grown from the detection point has substantial overlap with the radiologist segmentation.
Figure 3B:
Figure 3C:
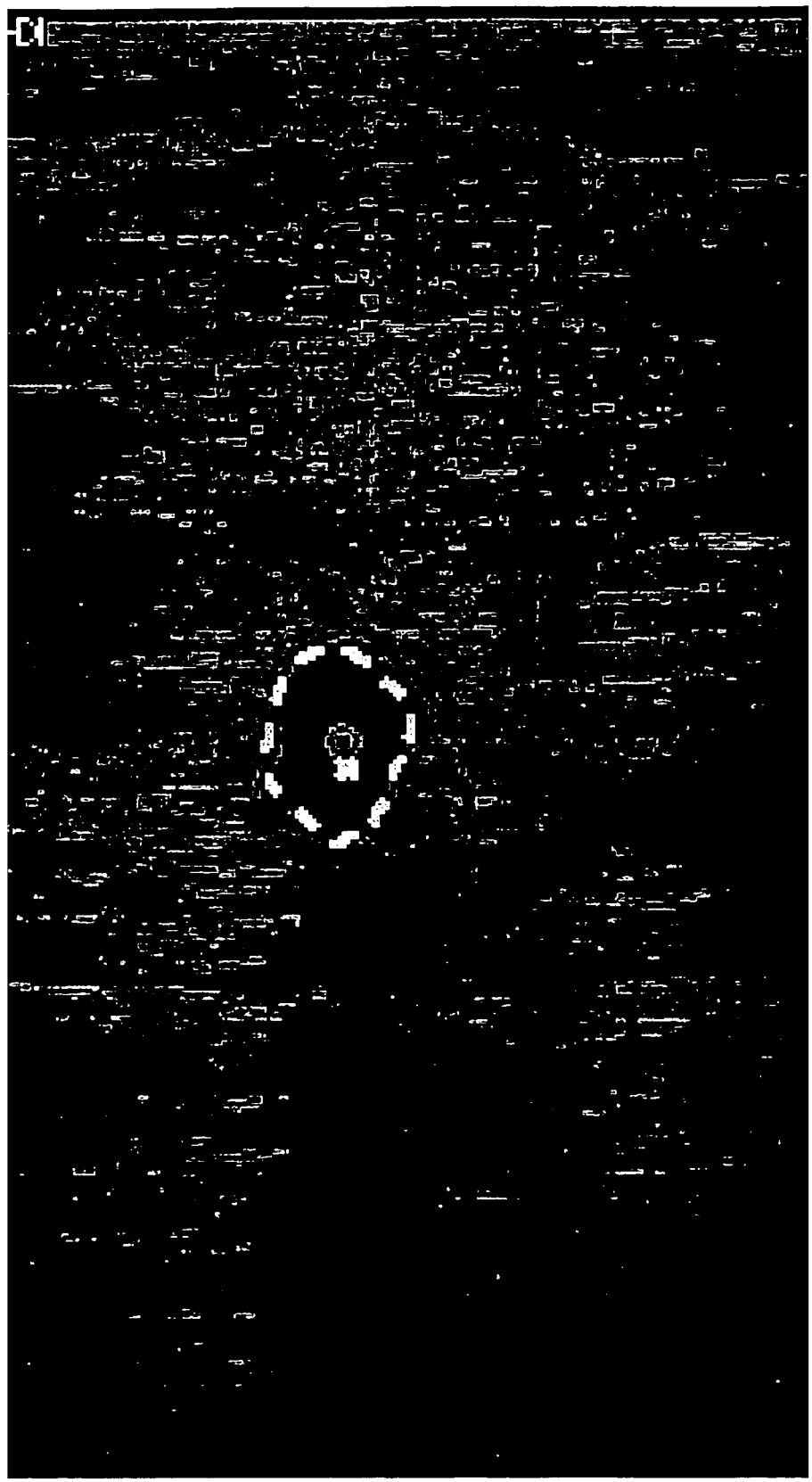
Figure 3D:
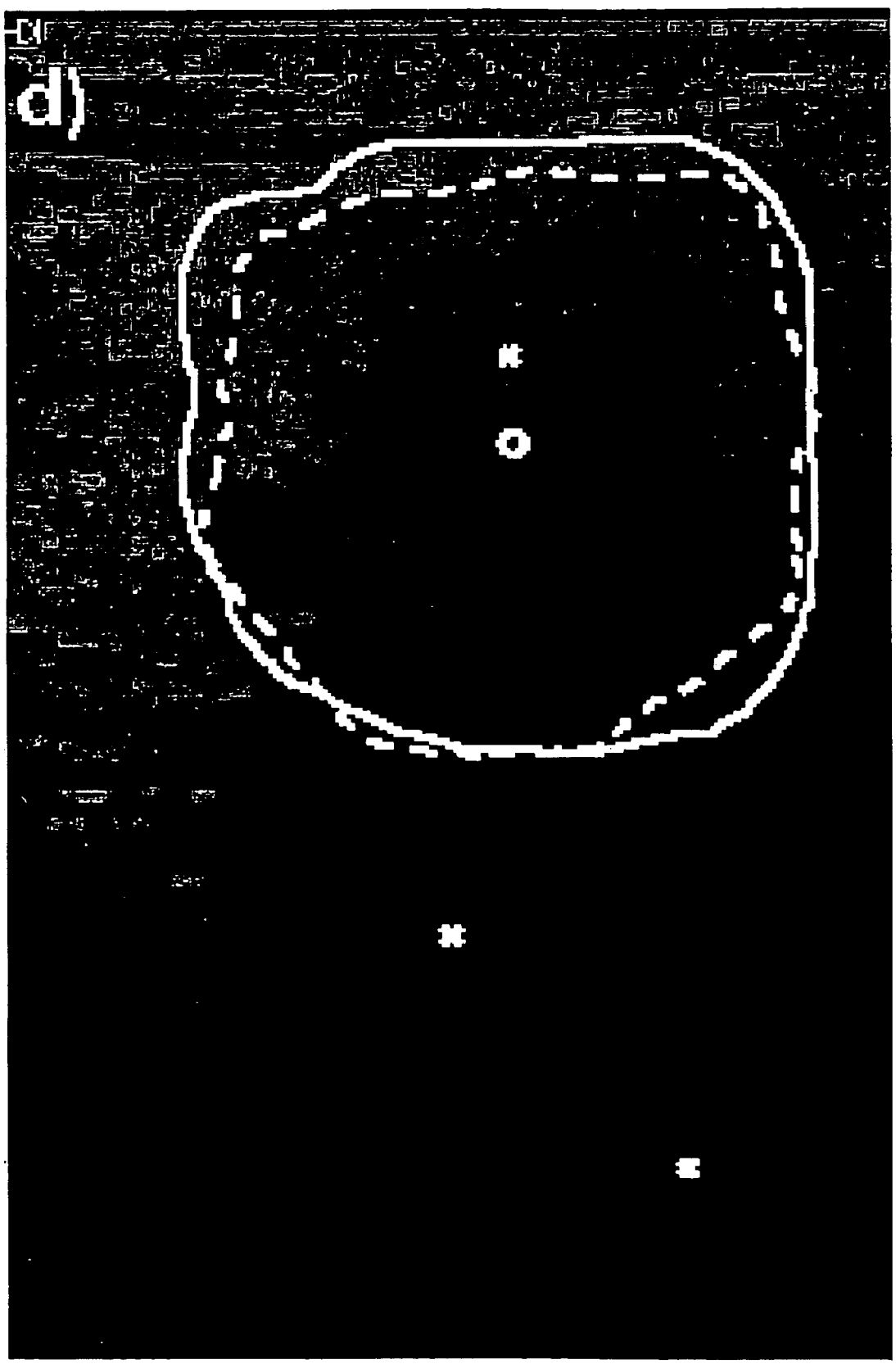
Figure 3E:
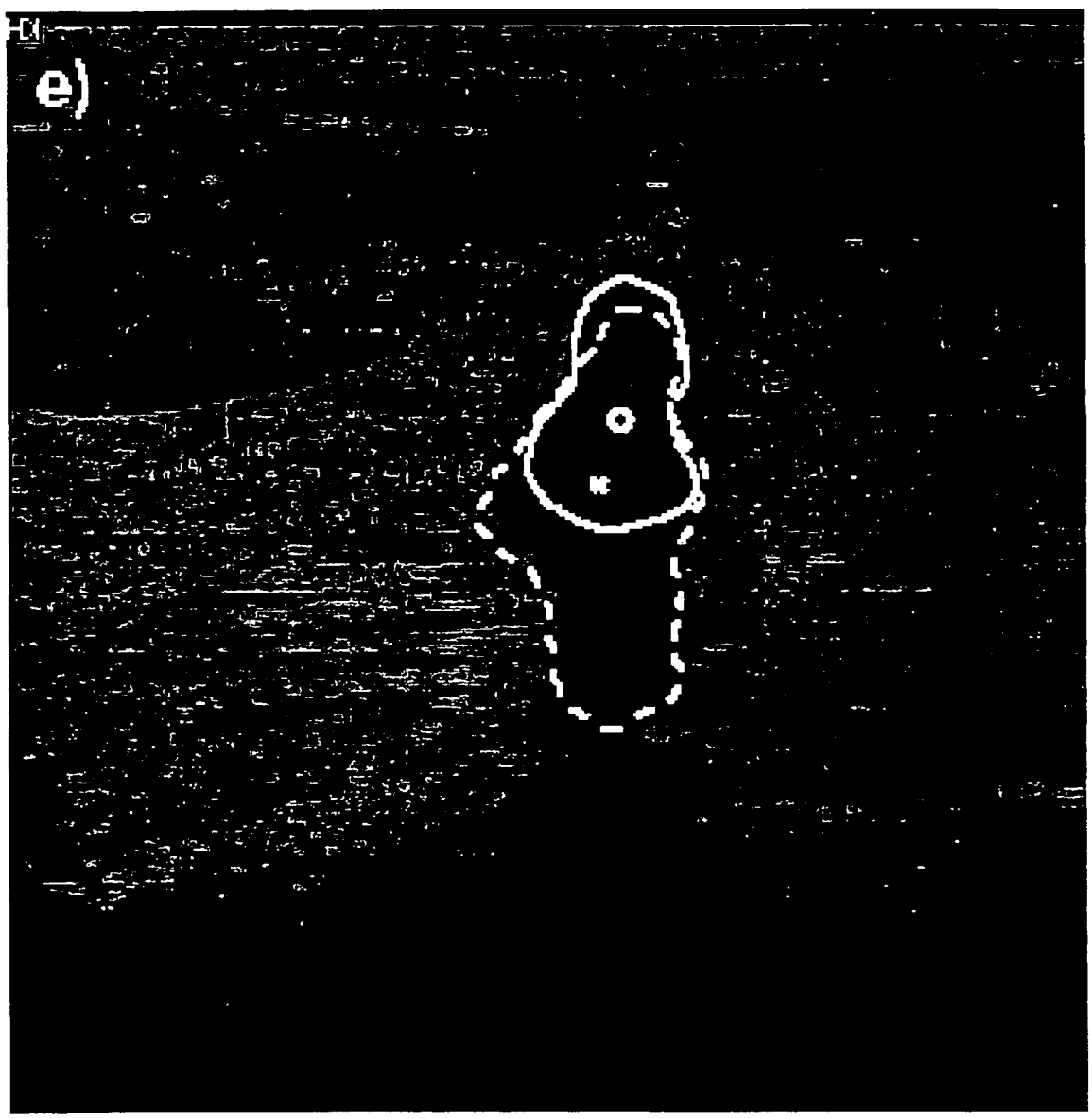
Figure 3F:
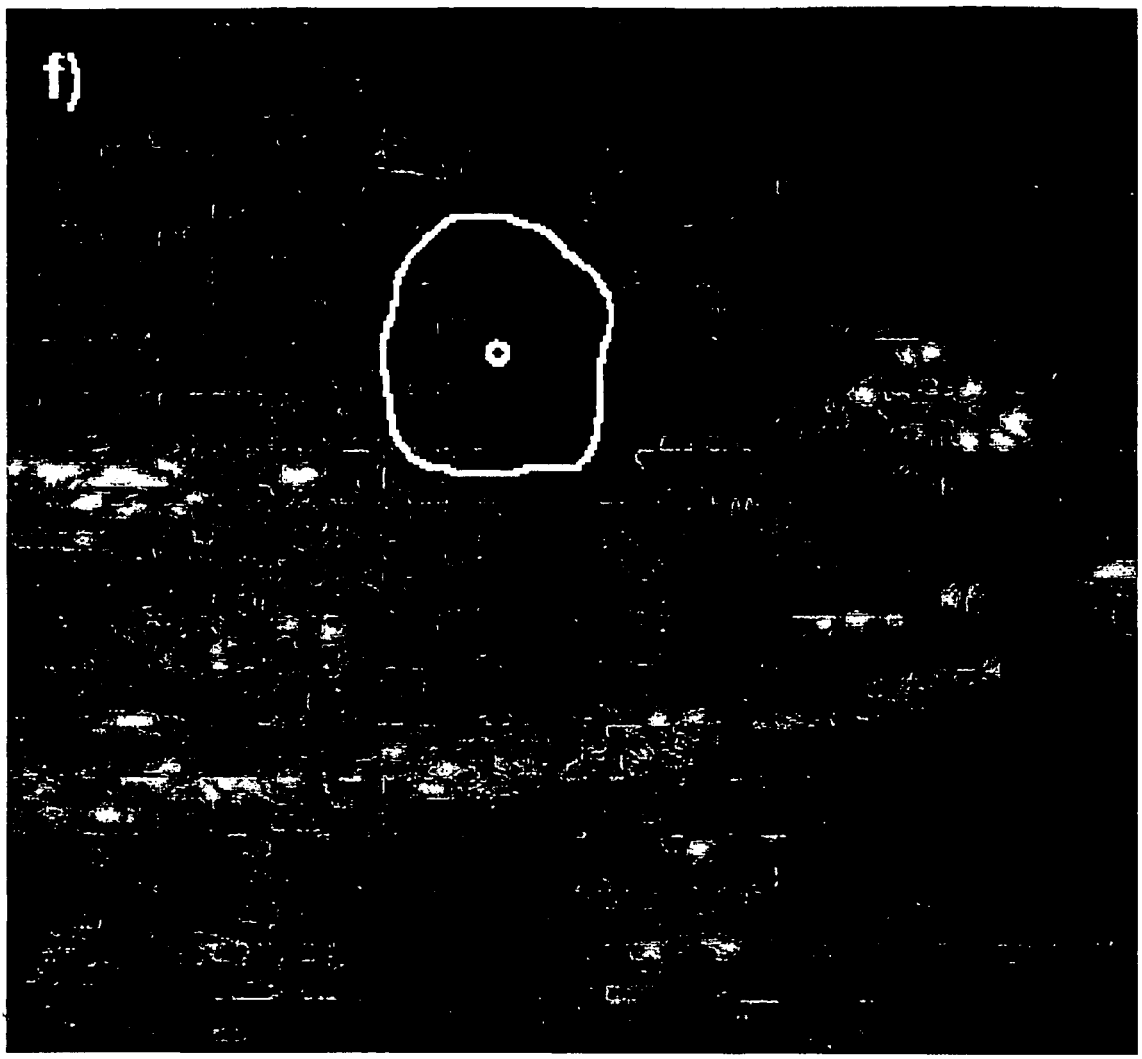
Figure 3G:
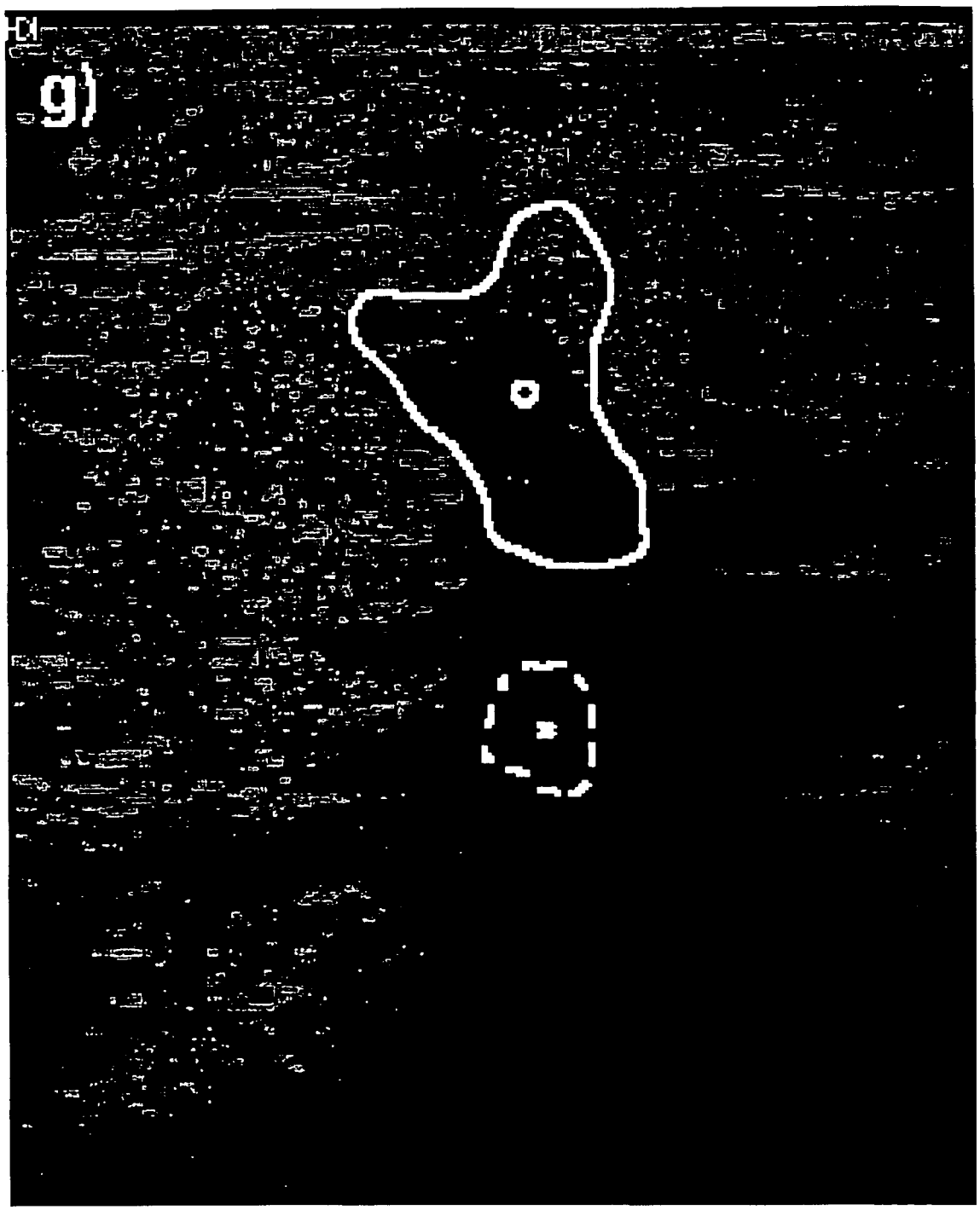
Figure 3H:
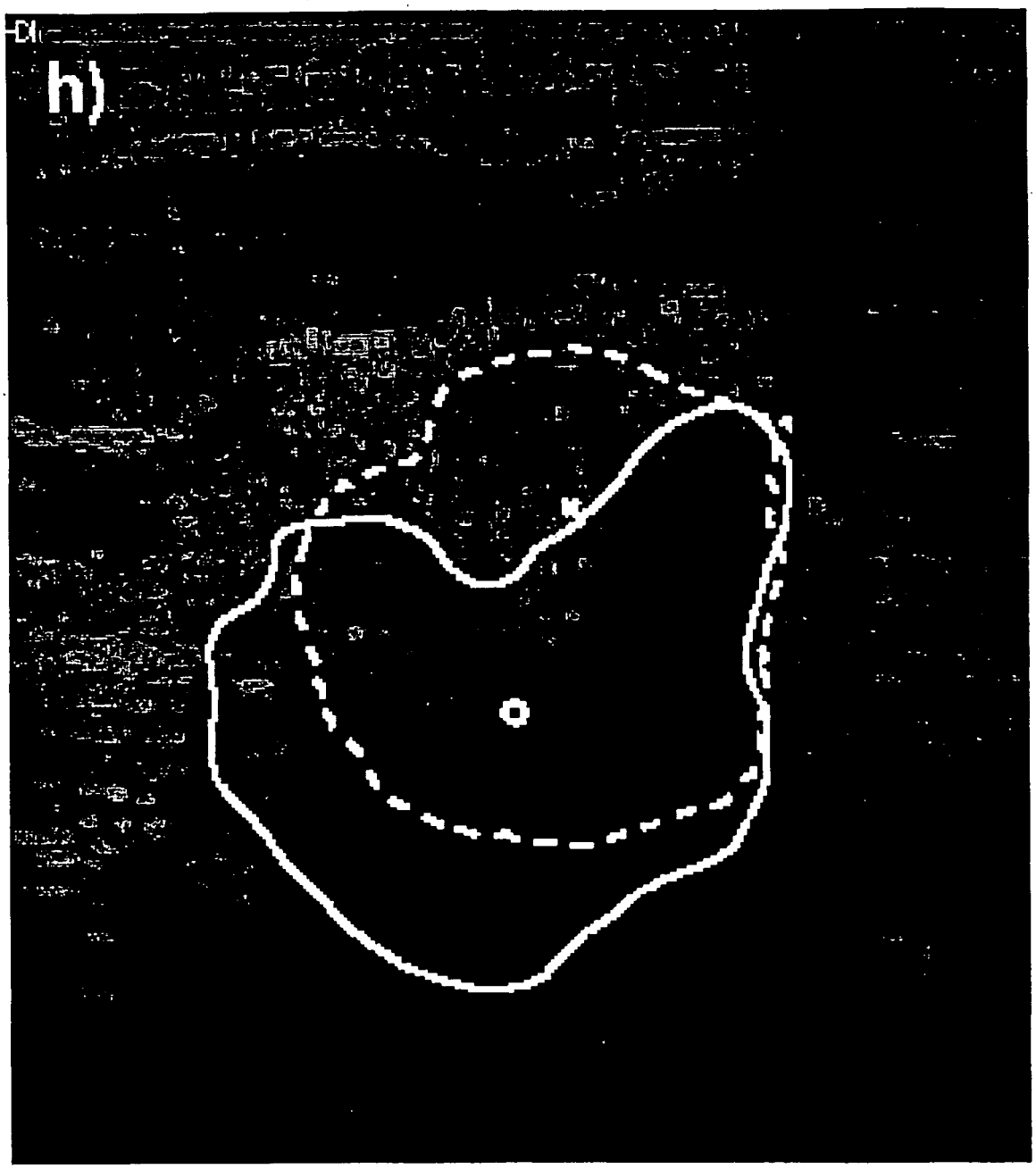

The variances in the width and depth direction for the Gaussian constraint function are varied adaptively and automatically for each image. After applying the Gaussian constraint function to the inverted preprocessed image, gray-value thresholding defines partitions whose margins are potential candidate abnormality margins. The potential margin that maximizes the utility function on the preprocessed image then defines the candidate abnormality margin. The utility function used in this segmentation algorithm is the Average Radial Derivative (ARD), shown in step S114, which gives the average directional derivative in the radial direction along the margin, $$ARD_i(\mu_x, \mu_y) = \frac{1}{N} \sum_{(x,y)\in C_i} \vec{g}(x, y) \bullet \hat{r}(x, y), \quad (14)$$

where N is the number of points in the contour $C_i$. The same constraining function is used to bias the region growing algorithm to abnormality-like contour shapes. The result is illustrated in FIG. 2(e). Once grown using ARD segmentation in step S114, various features are extracted in step S116, including abnormality shape, echogenic texture, and posterior acoustic enhancement or shadowing.

In the clinical evaluation of breast sonography, radiologists take into account features such as abnormality shape, margin sharpness, echogenic texture, posterior acoustic enhancement and shadowing (See Reference 23 and U.S. Pat. No. 5,984,870). Features of cysts, benign solid masses and malignant abnormalities differ to a large extent. Cysts are often hyperechogenic, show posterior acoustic enhancement, have sharp margins, and are wider than they are tall. Benign solids tend to be hyperechogenic, and may show posterior acoustic shadowing. Malignant masses tend to have unsharp margins, irregular shapes, are hypoechogenic, may show significant posterior acoustic shadowing, and may be taller than they are wide. Even though the feature characteristics differ, true abnormalities show strong features, while the spuriously grown regions from false detections show weak features, or uncommon feature combinations.

The detections, specifically the grown regions, are classified as true positive (TP) or false positive (FP) employing a Bayesian neural network (BNN). Analysis is performed using four similar features that are used to distinguish benign and malignant sonographic abnormalities: depth-to-width ratio, RGI value (obtained from Equation 1), texture, and posterior acoustic behavior of the candidate abnormality (See References 21 and 23). These features are extracted automatically in step S116.

In order to obtain the depth-to-width ratio (DWR), the following equation is applied:

$$DWR = \frac{Depth}{Width} = \frac{\max_j(\gamma_2(j)) - \min_j(\gamma_2(j))}{\max_j(\gamma_1(j)) - \min_j(\gamma_1(j))}, \quad (15)$$

where $j=(0,1,\ldots,J-1)$. Cysts and benign solids tend to be wider than they are deep and benign lesions, therefore, tend to yield smaller values for the DWR than malignant lesions.

Texture is quantified using the autocorrelation in depth of R. The gray level values in the minimal rectangular ROI containing the candidate abnormality, are used to define:

$$COR = \sum_{n=0}^{N_R-1} \frac{\overline{C}_y(n)}{\overline{C}_y(0)}, \quad (16)$$

where the autocorrelation in depth and its sum in the lateral direction are:

$$C_y(m,n) = \sum_{p=0}^{N_R-1-n} R^2(m, n+p)R^2(m,p), \quad (17)$$

$$\overline{C}_y(n) = \sum_{m=0}^{M_R-1-n} C_y(m,n). \quad (18)$$

Because the COR is a sum and not an average, it includes both texture information and size information.

Posterior acoustic behavior compares the gray-level values posterior to the candidate abnormality with the gray-level values of tissue adjacent to the candidate abnormality at the same depth. This comparison considers differences in the average gray level values of the appropriate ROI. To avoid edge shadows, the ROI is defined as the candidate abnormality itself minus a portion of the candidate abnormality's lateral sides. The left, post, and right ROIs are rectangular with the same width and area as the ROI which includes the candidate abnormality itself minus a portion of the candidate abnormality's lateral sides. The posterior acoustic behavior feature is the minimum side difference (MSD). The minimum is chosen in order to err on the side of malignancy. The posterior acoustic behavior is defined as:

$$MSD = \min(A_{post} - A_{left}, A_{post} - A_{right}), \quad (19)$$

where $A_{post}$, $A_{left}$, and $A_{right}$ are the average gray-level values over the appropriate ROI.

These feature values form the input for a Bayesian neural network (BNN) with five hidden layers and one output node in step S118. The output is a measure for the confidence that a given candidate abnormality is a true abnormality in step S120.

In the final stage, the likelihood that a given candidate abnormality represents an actual abnormality is calculated for all candidate abnormalities. Receiver Operator Characteristics (ROC) analysis was used to evaluate the BNN. (See Reference 26). The BNN outputs were validated using round-robin and jack-knife techniques.

The performance of the initial detection algorithm based on RGI filtering was assessed by determining whether or not the detected points fell within the radiologist abnormality outlines. Points within the contour were defined as TP detections, and those that fell outside the contour were defined as FP detections. The results are summarized in Table 1. Table 1 demonstrates the performance as a function of the lower boundary of the RGI threshold value, and the resulting true-positive and false-positive detections. For the majority of images, an RGI threshold value of 0.74 resulted in detection points. For less than 30% of the images, the RGI threshold value was iteratively lowered. The number of FPs increased as the RGI threshold value was lowered to obtain a detection. Analysis of the entire database (757 images) at a fixed threshold of 0.74 resulted in a true-positive fraction (TPF) of only 0.66 (by image, at 0.41 FP/image). By use of this iterative threshold method, a TPF of 0.87 at an FP/image of 0.76 was obtained. Moreover, the iterative thresholding method resulted in substantially lower FP rates than would be obtained by employing a fixed lower value for the RGI threshold of 0.62, which resulted in a TPF 0.89 at a cost of 2.0 FP/image.

TABLE 1

| RGI Threshold | Number of Images Analyzed | Overall TPF | Overall FP/image |
|---|---|---|---|
| 0.74 | 536 | 0.66 | 0.41 |
| 0.7 | 98 | 0.76 | 0.54 |
| 0.66 | 87 | 0.83 | 0.68 |
| 0.62 | 36 | 0.87 | 0.76 |

Table 2 discloses the detection performance for different types of abnormalities. TP detections are given both per image and per case. Complex cysts were the easiest to detect by RGI filtering, with a TPF by image and TPF by case being almost identical, indicating that cysts are usually well visible in multiple images of a given case. The ease of detection was also reflected in the low number of FP detections per image. Since cysts tend to be round and well-defined in an image, they were found at the highest RGI threshold value. For benign solid masses the TP detection rate is lower than for cysts, due to the presence of complicated image features such as vague abnormality edges, irregular abnormality shapes and post-abnormality shadowing. The difference between true detections by case and by image was larger, illustrating the importance of viewing irregularly shaped 3D objects from different angles when limited to a 2D imaging technique.

Malignant abnormalities are by far the hardest to detect. They are often highly irregular in shape, sometimes extremely small, and often extensive shadowing complicates detection. The high FP detection rate illustrated that malignant abnormalities look more like non-abnormality image structures. More effort, i.e., iterative lowering of the RGI threshold value, is often necessary to determine ROIs in images with subtle abnormalities, resulting in detection of both abnormality and non-abnormality regions. On the other hand, shadows are very prominent in a large number of these images, resulting in multiple detection points within the abnormality shadows at the highest threshold value. For malignant abnormalities, the difference in TP detection on a by image and a by case basis is the largest, as expected from the complicated image features for malignant abnormalities.

The number of images and cases that did not result in any false detections was also of interest, especially in a screening environment, as shown in Table 2. The results for cysts and benign solid masses are almost identical. For malignant abnormalities, still almost half of the images had no FP detections, suggesting that FP detections tend to occur in groups, perhaps due to characteristics of the sonographic parenchymal pattern.

TABLE 2

| Image Set | TPF by image | TPF by case | FP/image | % without FPs by image | % without FPs by case |
|---|---|---|---|---|---|
| entire database | 0.87 | 0.93 | 0.76 | 53 | 39 |
| cysts | 0.95 | 0.97 | 0.64 | 55 | 40 |
| benign solid | 0.86 | 0.92 | 0.77 | 54 | 41 |
| malignant | 0.78 | 0.87 | 0.88 | 49 | 35 |

Analysis of the 36 constructed "normal" images resulted in 6 FP detections (0.17 FP/image). When taking into consideration that these constructed images are a factor of 3 smaller on average than the database images, an estimate of 0.51 FP/image for average sized normal images was obtained. This was considerably lower than the 0.76 FP/image found for the entire database, and probably due to edge effects. These results confirm that this approach does not introduce many FP detections in normal images.

Examples of automated detection and segmentation are shown in FIG. 3, (a)–(h). Some sonographic characteristics, extensive shadowing behind abnormalities in particular, make abnormality detection and/or segmentation more difficult. Shadows often occur behind malignant and benign solid abnormalities because of the abnormalities' sound absorbing properties. These dark regions can be mistaken for additional abnormalities and frequently lead to FP detections, as illustrated in FIG. 3(d). Moreover, in some cases the abnormality shadow is the most prominent entity in an image, while the abnormality itself is vague, which results in detection of the shadow rather than of the abnormality itself. Even when an abnormality is detected, shadowing may influence the region growing and cause part of the shadow to be segmented along with the abnormality as illustrated in FIG. 3(e). Edge shadows, with or without posterior acoustic enhancement as often seen for cysts, do not seem to cause any problems for this detection and segmentation procedure.

In order to distinguish FPs from abnormalities, it was discovered that a BNN was very useful. For this purpose, the database was divided in half: half of the cases for each abnormality type were used for training, the other half for testing. A seven-layer BNN was designed, with an input layer, an output layer, and five hidden layers. The input units represented selected features extracted from the abnormalities, the single output unit is a likelihood of a true abnormality. While varying numbers of hidden layers were evaluated through experimentation, five is the preferred number. It is expected that the likelihood of true abnormality correlates well with a radiologist's determination. Similarly, classifiers such as linear discriminants and artificial neural networks (ANNs) may also be used to determine the likelihood of a true abnormality.

Various combinations of features for inputs were tested for the determination of a likelihood of true abnormality. (See U.S. Pat. No. 5,984,870).

Figure 4:
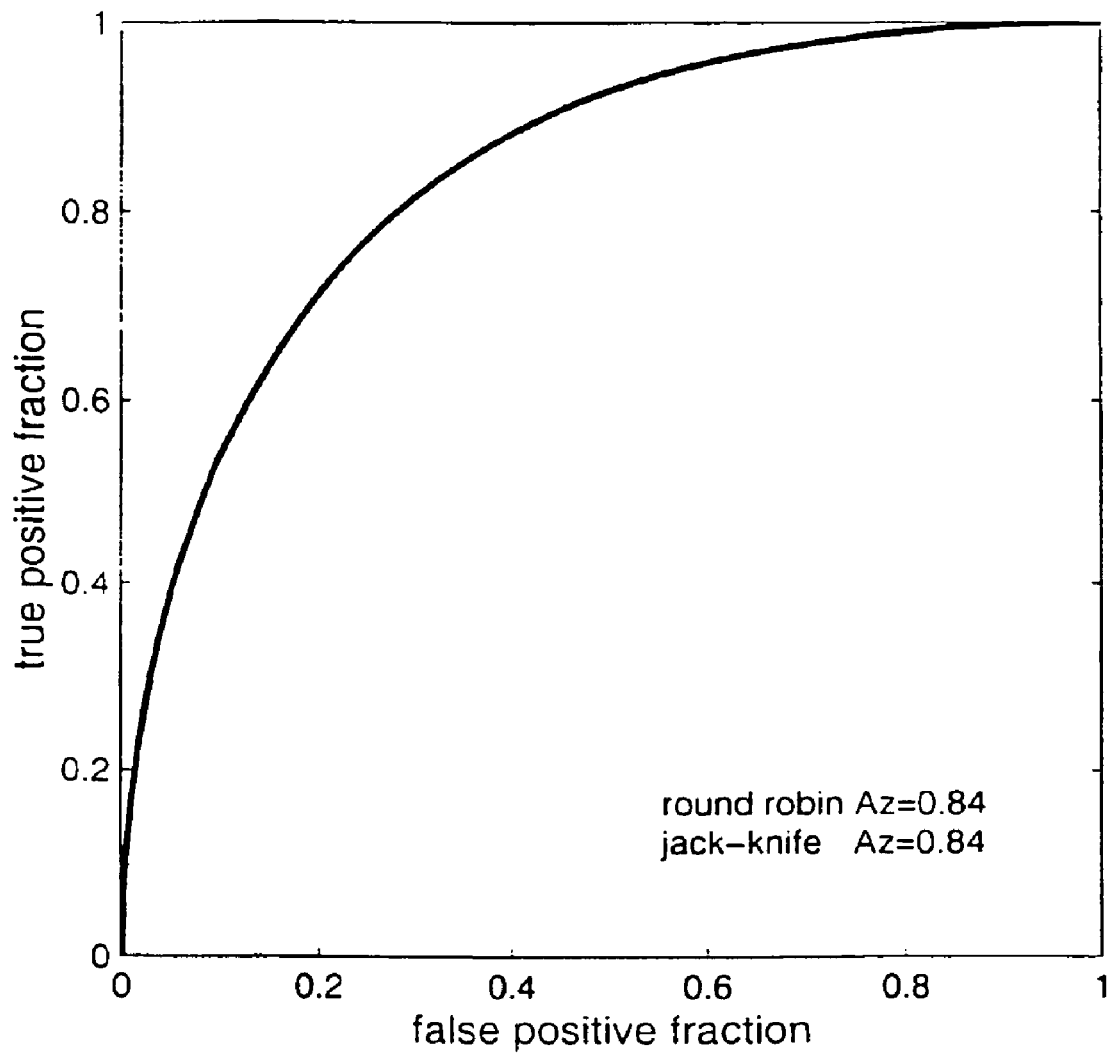
FIG. 4 illustrates Receiver Operator Characteristics (ROC) analysis of BNN performance.

In order to evaluate the peformance of the BNN in distinguishing abnormalities from FPs, jack-knife analysis was used. The database was split in half ten (10) times, where each time half of the cases for each abnormality type were randomly selected for training and the other half was used for testing. The ROC curves used to classify the detected abnormality sites as cancerous or not cancerous are shown in FIG. 4. The $A_z$ values (area under the ROC curve and a measure for performance) are 0.88 and 0.82 for training and testing, respectively. The difference in the $A_z$ values resulted from suspected slight over-training of the network, and the fact that the randomly selected training set was easier than the set used for testing (obvious when training and testing set are interchanged; $A_z$ values of 0.86 and 0.83 were obtained, respectively, for training and testing).

Subsequently, a round-robin analysis was performed for the entire database. Here, each case was singled out sequentially for testing, while the BNN was trained on the remaining cases. This resulted in an $A_z$ value of 0.84, which was comparable to the performance found for distinguishing different abnormality types in sonography using linear discriminant analysis (based on feature analysis of regions grown from the center of the radiologist segmented abnormality). (See References 21 and 23). The detection results for various thresholds of the BNN are shown in Table 3.

TABLE 3

BNN Thresholds

| BNN threshold | FPF | TPF by image | TPF by case | FP/image |
|---|---|---|---|---|
| 0.23 | 0.6 | 0.86 | 0.93 | 0.34 |
| 0.06 | 0.8 | 0.89 | 0.94 | 0.48 |
| 0 | 1 | 0.9 | 0.95 | 0.61 |

The overall performance of the method is summarized in Table 4 below.

TABLE 4

Summary of Performance After Each Stage

| Stage | TPF by image | TPF by case | FP/image |
|---|---|---|---|
| RGI filtering and iterative thresholding procedure | 0.87 | 0.93 | 0.76 |
| ARD region growing (segmentation) | 0.9 | 0.95 | 0.61 |
| BNN classifier (at FPF = 0.8) | 0.89 | 0.94 | 0.48 |

In summary, the computer-aided scheme for determining the location of abnormalities in medical images can be implemented based on the likelihood of abnormality defined above. First, a database of medical images with a variety of abnormalities is created, from which many pairs of similar images are selected. The locations and likelihood of malignancy are determined and the BNN is trained by use of the determinations and a number of features extracted from the candidate abnormality.

Computer and System

This invention conveniently may be implemented using a conventional general purpose computer or micro-processor programmed according to the teachings of the present invention, as will be apparent to those skilled in the computer art. Appropriate software can readily be prepared by programmers of ordinary skill based on the teachings of the present disclosure, as will be apparent to those skilled in the software art.

As disclosed in cross-referenced U.S. patent application Ser. No. 09/818,831, a computer implements the method of the present invention, wherein the computer housing houses a motherboard which contains a CPU, memory (e.g., DRAM, ROM, EPROM, EEPROM, SRAM, SDRAM, and Flash RAM), and other optical special purpose logic devices (e.g., ASICS) or configurable logic devices (e.g., GAL and reprogrammable FPGA). The computer also includes plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

As stated above, the system includes at least one computer readable medium. Examples of computer readable media are compact discs, hard disks, floppy disks, tape, magneto-optical disks, PROMs (e.g., EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Such computer readable media further includes the computer program product of the present invention for performing the inventive method herein disclosed. The computer code devices of the present invention can be any interpreted or executable code mechanism, including but not limited to, scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of detecting a candidate abnormality in a sonographic medical image, comprising the steps of:
   obtaining a sonographic medical image;
   determining a radial gradient index (RGI) at plural pixels to produce an RGI image;
   thresholding the RGI image;
   determining a candidate abnormality in the RGI image based on the thresholding step;
   locating a center point of the candidate abnormality in the RGI image and a corresponding center point in the sonographic image; and
   segmenting the candidate abnormality in the sonographic image to identify a margin of the candidate abnormality, said segmenting including identifying a plurality of potential candidate margins based on the center point in the sonogranhic image, determining an average radial derivative for each of the plurality of potential candidate margins, and selecting the margin of the candidate abnormality from the plurality of potential candidate margins based on the determined average radial derivative.

2. The method of claim 1, further comprising:
   extracting plural features from the segmented candidate abnormality; and
   determining a likelihood of the candidate abnormality being an actual abnormality based on the extracted plural features.

3. The method of claim 2, wherein the extracting steps comprises:
   extracting at least four features from the group comprising candidate abnormality shape, margin sharpness, echogenic texture, RGI value, posterior acoustic enhancement, and shadowing.

4. The method of claim 2, wherein the determining a likelihood step comprises:
   using a classifier; and
   determining a likelihood of the candidate abnormality being an actual abnormality based on the output of the classifier.

5. The method of claim 4, wherein the using step comprises:
   using a Bayesian Neural Network (BNN).

6. The method of claim 5, wherein the using the BNN step comprises:
   using a BNN having between 3 and 7 hidden layers.

7. The method of claim 5, wherein the using the BNN step comprises: using a BNN having 7 layers, comprised of an input layer, and output layer, and 5 hidden layers.

8. The method of claim 4, wherein the using step comprises:
   using an artificial neural network (ANN).

9. The method of claim 4, wherein the using step comprises:
   using linear discriminants.

10. The method of claim 1, wherein the thresholding step comprises: interatively thresholding the RGI image.

11. A system implementing a method of detecting a candidate abnormality in a sonographic medical image, said method comprising steps of:
   obtaining a sonographic medical image;
   determining a radial gradient index (RGI) at plural pixels to produce an RGI image;
   thresholding the RGI image;
   determining a candidate abnormality in the RGI image based on the thresholding step;
   locating a center point of the candidate abnormality in the RGI image and a corresponding center point in the sonographic image; and segmenting the candidate abnormality in the sonographic image to indentify a margin of the candidate abnormality, said segmenting including identifying a plurality of potential candidate margins based on the center point in the sonographic image, determining an average radial derivative for each of the plurality of potential candidate margins, and selecting the margin of the candidate abnormality from the plurality of potential candidate margins based on the determined average radial derivative.

12. A computer program product storing program code for execution on a computer system, said program code including:

a first program code to obtain a sonographic medical image;

a second program code to determine a radial gradient index (RGI) at plural pixels to produce an RGI image;

a third program code to threshold the RGI image;

a fourth program code to determine a candidate abnormality in the RGI image based on the thresholding step;

a fifth program code to locate a center point of the candidate abnormality in the RGI image and a corresponding center point in the sonographic image; and a sixth program code to segment the candidate abnormality in the sonographic image to identify a margin of the candidate abnormality, said sixth program code including identifying a plurality of potential candidate margins based on the center point in the sonographic image, determining an average radial derivative for each of the plurality of potential candidate margins, and selecting the margin of the candidate abnormality from the plurality of potential candidate margins based on the determined average radial derivative.

13. The computer program product of claim 12, further comprising:

a seventh program code to extract plural features from the segmented candidate abnormality; and an eighth program code to determine a likelihood of the candidate abnormality being an actual abnormality based on the extracted plural features.

14. The computer program product of claim 13, wherein the seventh program code comprises:

an ninth program code to extract at least four features from the group comprising candidate abnormality shape, margin sharpness, echogenic texture, RGI value, posterior acoustic enhancement, and shadowing.

15. The computer program product of claim 13, wherein the eighth program code comprises:

a ninth program code to use a classifier; and a tenth program code to determine a likelihood of the candidate abnormality being an actual abnormality based on the output of the classifier.

16. The computer program product of claim 15, wherein the ninth program code comprises:

an eleventh program code to use a Bayesian Neural Network (BNN).

17. The computer program product of claim 16, wherein the eleventh program code comprises:

a twelfth program code to use a BNN having between 3 and 7 hidden layers.

18. The computer program product of claim 16, wherein the eleventh a twelfth program code to use a BNN having 7 layers, comprised of an input layer, and output layer, and 5 hidden layers.

19. The computer program product of claim 15, wherein the ninth program code comprises:

an eleventh program code to use an artificial neural network (ANN).

20. The computer program product of claim 15, wherein the ninth program code comprises:

an eleventh program code to use linear discriminants.

21. The computer program product of claim 12, wherein the third program code comprises:

a seventh program code to iteratively threshold the RGI image.

* * * * *